(12) United States Patent
Ishimatsu et al.

(10) Patent No.: US 8,257,972 B2
(45) Date of Patent: Sep. 4, 2012

(54) CELL TRANSFORMED BY HUMAN WNT3A GENE

(75) Inventors: Yumiko Ishimatsu, Yokohama (JP);
Shunsuke Iriyama, Yokohama (JP);
Shigeyoshi Fujiwara, Yokohama (JP);
Tsutomu Soma, Yokohama (JP); Jiro Kishimoto, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 12/735,473

(22) PCT Filed: Jan. 21, 2009

(86) PCT No.: PCT/JP2009/050884
§ 371 (c)(1),
(2), (4) Date: Jul. 20, 2010

(87) PCT Pub. No.: WO2009/093612
PCT Pub. Date: Jul. 30, 2009

(65) Prior Publication Data
US 2010/0311163 A1  Dec. 9, 2010

(30) Foreign Application Priority Data
Jan. 21, 2008 (JP) ................. 2008-010823

(51) Int. Cl.
*C12N 5/071* (2010.01)
*C12N 5/00* (2006.01)
(52) U.S. Cl. ........................ 435/366; 435/325
(58) Field of Classification Search .............. None
See application file for complete search history.

(56) References Cited

U.S. PATENT DOCUMENTS
7,175,842 B2 * 2/2007 Morgan et al. ............... 424/93.7

FOREIGN PATENT DOCUMENTS
| JP | 2000-000089 A | 1/2000 |
| JP | 2008-029331 A | 2/2008 |
| WO | WO 01/74164 A1 | 10/2001 |

OTHER PUBLICATIONS

Brondyk, B. pTarget™ Vector: A Mammalian Expression T-Vector, Promega Notes Magazine, No. 58, 1996, p. 02.*
Verras et al. Wnt3a Growth Factor Induces Androgen Receptor-Mediated Transcription and Enhances Cell Growth in Human Prostate Cancer Cells. Cancer Research. vol. 64, Dec. 15, 2004, p. 8860-8866.*
Wong et al. Differential Transformation of Mammary Epithelial Cells by Wnt Genes. Molecular and Cellular Biology. Sep. 1994, p. 6278-6286.*
International Search Report mailed Mar. 3, 2009, in PCT/JP2009/050884, 2 pages.
Almeida et al., "Wnt Proteins Prevent Apoptosis of Both Uncommitted Osteblast Progenitors and Differentiated Osteoblasts by β-Catenin-dependent and -independent Signaling Cascades Involving Src/ERK and Phosphatidylinositol 3-Kinase/AKT," J. Biol. Chem., Dec. 16, 2005, 280(50):41342-41351.
Kishimoto et al., "Wnt signaling maintains the hair-inducing activity of the dermal papilla," Genes & Development, 2000, 14(10):1181-1185.
Rawadi et al., "BMP-2 Controls Alkaline Phosphatase Expression and Osteoblast Mineralization by a Wnt Autocrine Loop," Journal of Bone and Mineral Research, 2003, 18(10):1842-1853.
Soma et al., "Recent progress of hair biology and regeneration of human hair follicle," Organ Biology, 2005, 12(4):311-322, (only the abstract is in English).
Krause et al., "Biology of the Hair Follicle: The Basics," Semin. Cutan. Med. Surg., Mar. 1, 2006, 25(1):2-10.
Saitoh et al., "Molecular Cloning and Characterization of WNT3A and WNT14 Clustered in Human Chromosome 1q42 Region," Biochemical and Biophysical Research Communications, 2001, 284:1168-1175.
Zhu et al., "Analysis of Wnt Gene Expression in Prostate Cancer: Mutual Inhibition by WNT11 and the Androgen Receptor," Cancer Research, Nov. 1, 2004, 64:7918-7926.

* cited by examiner

*Primary Examiner* — Jennifer Dunston
*Assistant Examiner* — Channing S Mahatan
(74) *Attorney, Agent, or Firm* — Foley & Lardner LLP

(57) ABSTRACT

Disclosed is a cell transformed by a vector containing human Wnt3a gene, wherein the cell is selected from a group consisting of hair follicle-derived cells and prostate cancer-derived cells.

2 Claims, 3 Drawing Sheets

Fig.1  HUMAN WNT3A GENE SEQUENCE

WNT3A Order cDNA clone, Links

Official Symbol WNT3A and Name: wingless-type MMTV integration site family, member 3A [Homo sapiens]

Other Aliases: MGC119418, MGC119419, MGC119420

Chromosome: 1; Location: 1q42

Annotation: Chromosome 1, NC_000001.9 (226261375..226315584)

MIM: 606359

GeneID: 89780

```
   1 agctcccagg gcccggcccc ccccggcgct cacgctctcg gggcggactc ccggccctcc
  61 gcgccctctc gcgcggcgat ggccccactc ggatacttct tactcctctg cagcctgaag
 121 caggctctgg gcagctaccc gatctggtgg tcgctggctg ttgggccaca gtattcctcc
 181 ctgggctcgc agcccatcct gtgtgccagc atcccgggcc tggtccccaa gcagctccgc
 241 ttctgcagga actacgtgga gatcatgccc agcgtggccg agggcatcaa gattggcatc
 301 caggagtgcc agcaccagtt ccgcggccgc cggtggaact gcaccaccgt ccacgacagc
 361 ctggccatct tcgggccgt gctggacaaa gctaccaggg agtcggcctt tgtccacgcc
 421 attgcctcag ccggtgtggc ctttgcagtg acacgctcat gtgcagaagg cacggccgcc
 481 atctgtggct gcagcagccg ccaccagggc tcaccaggca agggctggaa gtggggtggc
 541 tgtagcgagg acatcgagtt tggtgggatg gtgtctcggg agttcgccga cgcccgggag
 601 aaccggccag atgcccgctc agccatgaac cgccacaaca cgaggctggg gcgccaggcc
 661 atcgccagcc acatgcacct caagtgcaag tgccacgggc tgtcgggcag ctgcgaggtg
 721 aagacatgct ggtggtcgca acccgacttc cgcgccatcg gtgacttcct caaggacaag
 781 tacgacagcg cctcggagat ggtggtggag aagcaccggg agtcccgcgg ctgggtggag
 841 accctgcggc cgcgctacac ctacttcaag gtgcccacgg agcgcgacct ggtctactac
 901 gaggcctcgc ccaacttctg cgagcccaac cctgagacgg gctccttcgg cacgcgcgac
 961 cgcacctgca acgtcagctc gcacggcatc gacggctgcg acctgctgtg ctgcggccgc
1021 ggccacaacg cgcgagcgga gcggcgccgg gagaagtgcc gctgcgtgtt ccactggtgc
1081 tgctacgtca gctgccagga gtgcacgcgc gtctacgacg tgcacacctg caagtaggca
1141 ccggccgcgg ctcccctctg acggggcggg ccctgcctga gggtgggctt ttccctgggt
1201 ggagcaggac tcccacctaa acggggcagt actcctccct ggggcgggca ctcctccctg
1261 ggggtgggc tcctacctgg gggcagaact cctacctgaa ggcagggctc ctccctggag
1321 ctagtgtctc ctctctggtg gctgggctgc tcctgaatga ggcggagctc caggatgggg
1381 aggggctctg cgttggcttc tccctgggga cggggctccc ctggacagag gcggggctac
1441 agattgggcg gggcttctct tgggtgggac agggcttctc ctgcggggc gaggcccctc
1501 ccagtaaggg cgtggctctg ggtgggcggg cactaggta ggcttctacc tgcaggcggg
1561 gctcctcctg aaggaggcgg ggctctagga tggggcacgg ctctggggta ggctgctccc
1621 tgagggcgga gcgcctcctt aggagtgggg tttatggtg gatgaggctt cttcctggat
1681 ggggcagagc ttctcctgac cagggcaagg cccttccac gggggctgtg gctctgggtg
1741 ggcgtggcct gcataggctc cttcctgtgg gtggggcttc tctgggacca ggctccaatg
1801 gggcggggct tctctccgcg ggtgggactc ttccctggga accgccctcc tgattaaggc
1861 gtggcttctg caggaatccc ggctccagag caggaaattc agcccaccag ccacctcatc
1921 cccaaccccc tgtaaggttc catccacccc tgcgtcgagc tgggaaggtt ccatgaagcg
1981 agtcgggtcc ccaacccgtg ccctgggat ccgagggccc ctctccaagc gcctggcttt
2041 ggaatgctcc aggcgcgccg acgcctgtgc caccccttcc tcagcctggg gtttgaccac
2101 ccacctgacc aggggcccta cctggggaaa gcctgaaggg cctcccagcc cccaacccca
2161 agaccaagct tagtcctggg agaggacagg gacttcgcag aggcaagcga ccgaggccct
2221 cccaaagagg cccgccctgc ccgggctccc acaccgtcag gtactcctgc cagggaactg
2281 gcctgctgcg cccaggccc cgcccgtctc tgctctgctc agctgcgccc ccttcttgc
2341 agctgcccag cccctcctcc ctgccctcgg gtctccccac ctgcactcca tccagctaca
2401 ggagagatag aagcctctcg tcccgtccct ccctttcctc cgcctgtcca cagccccta
2461 agggaaaggt aggaagagag gtccagcccc ccaggctgcc cagagctgct ggtctcattt
2521 gggggcgttc gggaggtttg gggggcatca acccccgac tgtgctgctc gcgaaggtcc
2581 cacagccctg agatgggccg gccccttcc tggcccctca tggcgggact ggagaaatgg
2641 tccgctttcc tggagccaat ggcccggccc ctcctgactc atccgcctgg cccgggaatg
2701 aatggggagg ccgctgaacc cacccggccc atatccctgg ttgcctcatg gccagcgccc
2761 ctcagcctct gccactgtga accggctcca acccctcaagg tgcggggaga agaacggcc
2821 aggcggggcg cccaagagc ccaaaagagg gcacaccgcc atcctctgcc tcaaattctg
2881 cgttttggt tttaatgtta tatctgatgc tgctatatcc actgtccaac gg
```

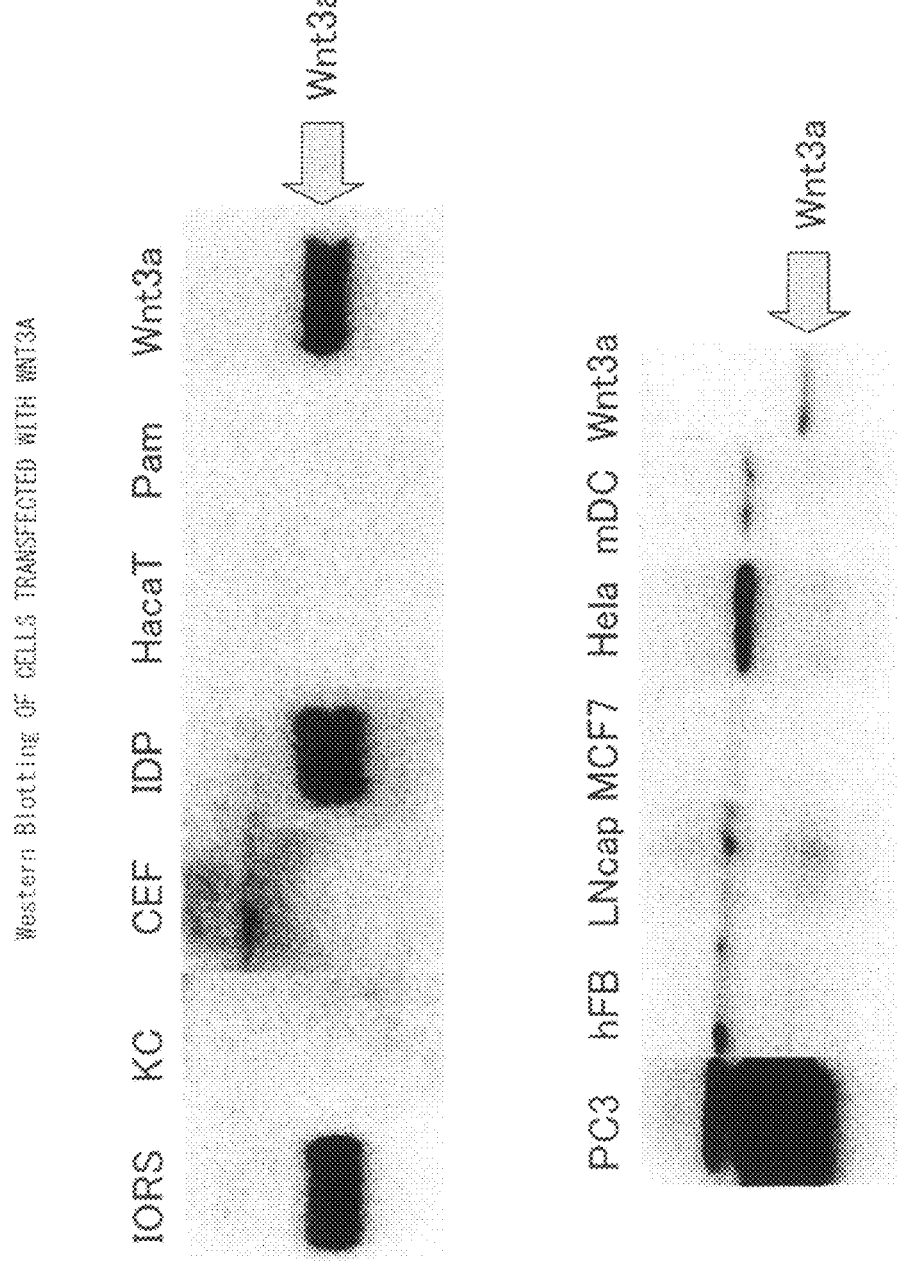

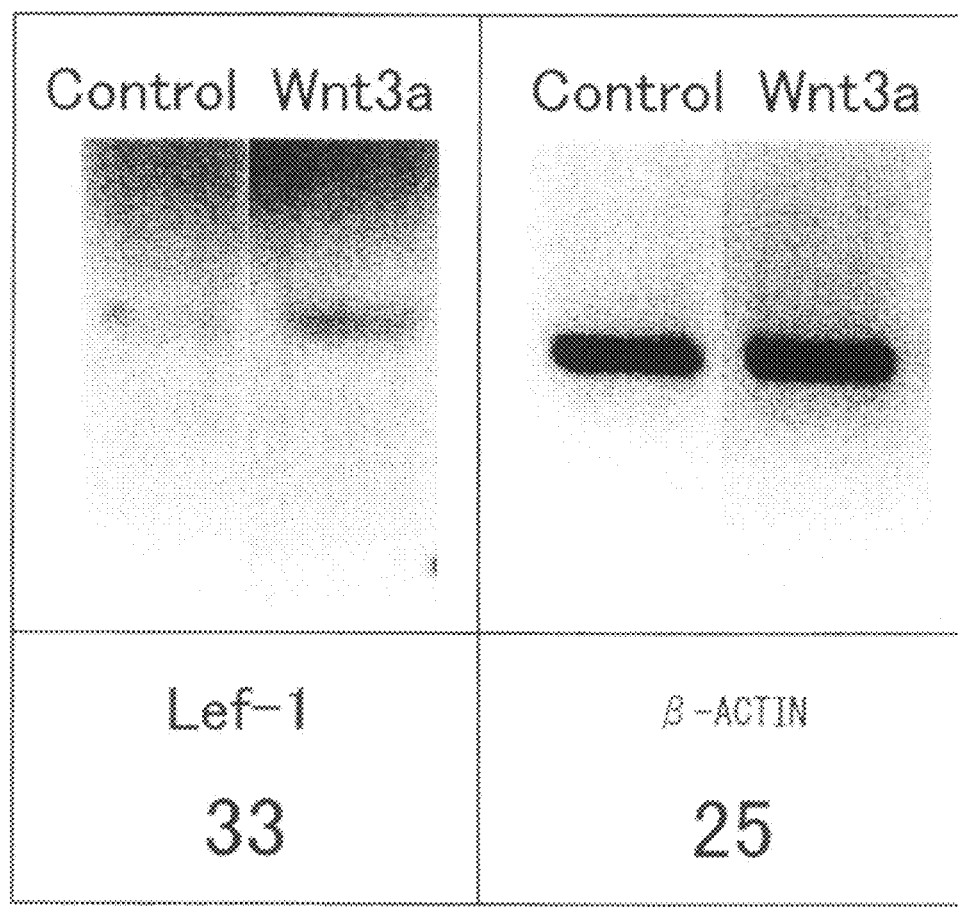

SEQUENCE LISTING

```
<160> NUMBER OF SEQ ID NOS: 7

<210> SEQ ID NO 1
<211> LENGTH: 2932
<212> TYPE: DNA
<213> ORGANISM: Homo sapiens

<400> SEQUENCE: 1
agctcccagg gcccggcccc cccggcgct  cacgctctcg gggcggactc ccggccctcc      60
gcgccctctc gcgcggcgat ggccccactc ggatacttct tactcctctg cagcctgaag     120
caggctctgg gcagctaccc gatctggtgg tcgctggctg ttgggccaca gtattcctcc     180
ctgggctcgc agcccatcct gtgtgccagc atcccgggcc tggtccccaa gcagctccgc     240
ttctgcagga actacgtgga gatcatgccc agcgtggccg agggcatcaa gattggcatc     300
caggagtgcc agcaccagtt ccgcggccgc cggtggaact gcaccaccgt ccacgacagc     360
ctggccatct tcgggcccgt gctggacaaa gctaccaggg agtcggcctt tgtccacgcc     420
attgcctcag ccggtgtggc ctttgcagtg acacgctcat gtgcagaagg cacggccgcc     480
atctgtggct gcagcagccg ccaccagggc tcaccaggca agggctggaa gtggggtggc     540
tgtagcgagg acatcgagtt tggtgggatg gtgtctcggg agttcgccga cgcccgggag     600
```

| | |
|---|---|
| aaccggccag atgcccgctc agccatgaac cgccacaaca acgaggctgg gcgccaggcc | 660 |
| atcgccagcc acatgcacct caagtgcaag tgccacgggc tgtcgggcag ctgcgaggtg | 720 |
| aagacatgct ggtggtcgca acccgacttc cgcgccatcg gtgacttcct caaggacaag | 780 |
| tacgacagcg cctcggagat ggtggtggag aagcaccggg agtcccgcgg ctgggtggag | 840 |
| accctgcggc cgcgctacac ctacttcaag gtgcccacgg agcgcgacct ggtctactac | 900 |
| gaggcctcgc ccaacttctg cgagcccaac cctgagacgg ctccttcgg cacgcgcgac | 960 |
| cgcacctgca acgtcagctc gcacggcatc gacggctgcg acctgctgtg ctgcggccgc | 1020 |
| ggccacaacg cgcgagcgga gcggcgccgg gagaagtgcc gctgcgtgtt ccactggtgc | 1080 |
| tgctacgtca gctgccagga gtgcacgcgc gtctacgacg tgcacacctg caagtaggca | 1140 |
| ccggccgcgg ctcccctgg acgggcggg ccctgcctga gggtgggctt ttccctgggt | 1200 |
| ggagcaggac tcccacctaa cgggcagt actcctccct gggggcggga ctcctccctg | 1260 |
| ggggtgggc tcctacctgg gggcagaact cctacctgaa gcagggctc ctccctggag | 1320 |
| ctagtgtctc ctctctggtg gctgggctgc tcctgaatga ggcggagctc caggatgggg | 1380 |
| aggggctctg cgttggcttc tccctgggga cggggctccc ctggacagag gcggggctac | 1440 |
| agattgggcg gggcttctct tgggtgggac agggcttctc ctgcggggc gaggcccctc | 1500 |
| ccagtaaggg cgtggctctg ggtgggcggg cactaggta ggcttctacc tgcaggcggg | 1560 |
| gctcctcctg aaggaggcgg ggctctagga tggggcacgg ctctgggta ggctgctccc | 1620 |
| tgagggcgga gcgcctcctt aggagtgggg ttttatggtg gatgaggctt cttcctggat | 1680 |
| ggggcagagc ttctcctgac cagggcaagg ccccttccac ggggctgtg gctctgggtg | 1740 |
| ggcgtggcct gcataggctc cttcctgtgg gtggggcttc tctgggacca ggctccaatg | 1800 |
| gggcggggct tctctccgcg ggtgggactc ttccctggga accgccctcc tgattaaggc | 1860 |
| gtggcttctg caggaatccc ggctccagag caggaaattc agcccaccag ccacctcatc | 1920 |
| cccaacccc tgtaaggttc catccacccc tgcgtcgagc tgggaaggtt ccatgaagcg | 1980 |
| agtcgggtcc ccaacccgtg ccctgggat ccgagggccc ctctccaagc gcctggcttt | 2040 |
| ggaatgctcc aggcgcgccg acgcctgtgc cacccctcc tcagcctggg gtttgaccac | 2100 |
| ccacctgacc aggggcccta cctgggaaa gcctgaaggg cctcccagcc cccaacccca | 2160 |
| agaccaagct tagtcctggg agaggacagg gacttcgcag aggcaagcga ccgaggcccct | 2220 |
| cccaaagagg cccgccctgc ccgggctccc acaccgtcag gtactcctgc cagggaactg | 2280 |
| gcctgctgcg ccccaggccc cgcccgtctc tgctctgctc agctgcgccc ccttctttgc | 2340 |
| agctgcccag cccctcctcc ctgccctcgg gtctccccac ctgcactcca tccagctaca | 2400 |
| ggagagatag aagcctctcg tcccgtccct cccttcctc cgcctgtcca cagcccctta | 2460 |
| agggaaaggt aggaagagag gtccagcccc ccaggctgcc cagagctgct ggtctcattt | 2520 |
| gggggcgttc gggaggtttg gggggcatca acccccgac tgtgctgctc gcgaaggtcc | 2580 |
| cacagccctg agatgggccg gcccccttcc tggcccctca tggcgggact ggagaaatgg | 2640 |
| tccgctttcc tggagccaat ggcccggccc ctcctgactc atccgcctgg cccgggaatg | 2700 |
| aatggggagg ccgctgaacc cacccggccc atatccctgg ttgcctcatg gccagcgccc | 2760 |
| ctcagcctct gccactgtga accggctccc accctcaagg tgcggggaga agaagcggcc | 2820 |
| aggcggggcg ccccaagagc ccaaaagagg gcacaccgcc atcctctgcc tcaaattctg | 2880 |
| cgttttggt tttaatgtta tatctgatgc tgctatatcc actgtccaac gg | 2932 |

<210> SEQ ID NO 2

```
<211> LENGTH: 18
<212> TYPE: DNA
<213> ORGANISM: Artificial
<220> FEATURE:
<223> OTHER INFORMATION: Wnt3a sense primer

<400> SEQUENCE: 2
gatggcccca ctcggata                                                   18

<210> SEQ ID NO 3
<211> LENGTH: 19
<212> TYPE: DNA
<213> ORGANISM: Artificial
<220> FEATURE:
<223> OTHER INFORMATION: Wnt3a antisense primer

<400> SEQUENCE: 3
ggtgcctact tgcaggtgt                                                  19

<210> SEQ ID NO 4
<211> LENGTH: 20
<212> TYPE: DNA
<213> ORGANISM: Artificial
<220> FEATURE:
<223> OTHER INFORMATION: Wnt3a sense primer

<400> SEQUENCE: 4
caggaactac gtggagatca                                                 20

<210> SEQ ID NO 5
<211> LENGTH: 20
<212> TYPE: DNA
<213> ORGANISM: Artificial
<220> FEATURE:
<223> OTHER INFORMATION: Wnt3a antisense primer

<400> SEQUENCE: 5
ccatcccacc aaactcgatg                                                 20

<210> SEQ ID NO 6
<211> LENGTH: 21
<212> TYPE: DNA
<213> ORGANISM: Artificial
<220> FEATURE:
<223> OTHER INFORMATION: Lef-1 sense primer

<400> SEQUENCE: 6
cttccttggt gaacgagtct g                                               21

<210> SEQ ID NO 7
<211> LENGTH: 20
<212> TYPE: DNA
<213> ORGANISM: Artificial
<220> FEATURE:
<223> OTHER INFORMATION: Lef-1 antisense primer

<400> SEQUENCE: 7
gtgttctctg gccttgtcgt                                                 20
```

CELL TRANSFORMED BY HUMAN WNT3A GENE

CROSS-REFERENCE TO RELATED APPLICATIONS

This application is a National Stage application of PCT/JP2009/050884, filed Jan. 21, 2009, which claims priority from Japanese application JP 2008-010823, filed Jan. 21, 2008.

TECHNICAL FIELD

The present invention provides a cell transformed with a vector containing human Wnt3a protein gene that demonstrates high expression efficiency of human Wnt3a protein.

BACKGROUND ART

Wnt protein is a secretory glycoprotein having a molecular weight of about 40,000 that is known to be an important intercellular signaling molecule for embryonic morphogenesis and hair follicle regeneration, and is involved in differentiation and functional maintenance of melanocytes. Nearly 20 types of vertebrate Wnt are known, these Wnt form subfamilies, and each binds to a seven-pass transmembrane receptor known as Frizzled and a single-pass transmembrane receptors known as LRP on the cell membrane. Wnt3a, which is a member of the Wnt family, has been clearly demonstrated on the basis of transplant studies in mice to maintain hair follicle formation induction activity of hair papilla by acting on hair papilla cells (Kishimoto, J. et al., Genes & Dev., 2000 May 15, 14(10), 1181-5), and considerable attention has recently been focused on its relationship with hair follicle induction. Research is being conducted on recombinant avian or mouse Wnt3a protein produced by avian Wnt3a or avian cells transformed with mouse Wnt3a gene by allowing this recombinant protein to act on mouse hair papilla cells.

When considering use in clinical studies applicable to humans, it is necessary to prepare large amounts of human Wnt3a recombinant protein instead of human or mouse protein. However, recombinant human Wnt3a has the problem of it being difficult to produce protein that retains adequate activity probably due to problems in translation and modification following transcription. Thus, selection of host cells for use in efficiently producing human Wnt3a recombinant protein that retains hair follicle induction activity is an important factor for elucidating the mechanisms of hair follicle formation and regeneration as well as screening and evaluating drugs that induce and accelerate hair follicle formation and regeneration.

Non-Patent Document 1: Genes & Dev., 2000 May 15, 14(10), 1181-5

DISCLOSURE OF THE INVENTION

Problems to be Solved by the Invention

An object of the present invention is to provide a cell capable of efficiently expressing human Wnt3a recombinant protein having activity that induces formation of hair follicles by hair papilla cells.

Means for Solving the Problems

As a result of conducting extensive studies, the inventors of the present invention found that hair follicle-derived cells and prostate cancer-derived cells are optimum as hosts for efficiently expressing human Wnt3a recombinant protein that retains activity, thereby leading to completion of the present invention.

Thus, the present application includes the following inventions:

(1) a cell transformed with a vector containing human Wnt3a gene, wherein the cell is selected from a group consisting of hair follicle-derived cells and prostate cancer-derived cells;
(2) the cell of (1), wherein the hair follicle-derived cells are IROS or IDP cells;
(3) the cell or (1), wherein the prostate cancer-derived cells are PC3 cells; and,
(4) the cell of any of (1) to (3), wherein the vector is a pTarget vector.

EFFECTS OF THE INVENTION

According to the present invention, human Wnt3a recombinant protein, which has activity that induces hair follicle formation by hair papilla cells, can be efficiently expressed, and elucidation of the mechanisms of hair follicle formation and regeneration, as well as evaluation of effective drugs for hair follicle regeneration, are expected to be carried out efficiently.

BRIEF DESCRIPTION OF THE DRAWINGS

FIG. 1 shows the nucleotide sequence of a gene encoding Wnt3a (SEQ ID NO:1).
FIG. 2 shows Western blotting of cells containing Wnt3a.
FIG. 3 shows confirmation of functional expression of Wnt3a introduced by accelerated expression of Lef-1.

BEST MODE FOR CARRYING OUT THE INVENTION

Human Wnt3a is a protein comprised of 352 amino acid residues, and the nucleotide sequence of a gene encoding this protein is shown in SEQ ID NO:1 and FIG. 1. An expression vector containing Wnt3a gene can be produced by linking Wnt3a gene to a vector through a suitable restriction site to be placed under the control of a suitable promoter of the vector using a known method. There are no particular limitations on the type of vector, and all types of commercially available vectors can be used, including commercially available animal cell expression vectors such as pTarget vector (Promega), pBK-CMV vector or pBK-RSV vector (Stratagene). pTarget vector is particularly preferable.

There are no particular limitations on a preferable promoter used in the present invention provided it is a suitable promoter corresponding to the host used to express gene, examples of which include CMV promoter, SRα promoter, SV40 promoter, LTR promoter, HSV-TK promoter and β-actin promoter.

In addition, an enhancer, splicing signal, poly(A) addition signal, selection marker or SV40 replication origin and the like may also be contained in the expression vector as desired.

Hair follicle-derived cells, such as human immortalized outer root sheath cells (IORS) or human immortalized dermal papilla cells (IDP), or human prostate cancer-derived cells (PC3) can be used as host cells. IORS are particularly preferable.

In order to obtain human outer root sheath cells, human scalp is obtained as a by-product of, for example, plastic surgery procedures or surgery procedures, and hair follicle tissue is obtained from the scalp under a stereo microscope.

Next, after treating the hair follicle tissue with a hydrolase solution, such as a mixed solution of collagenase and dispase, for 30 minutes at 37° C., the tissue is allowed to stand undisturbed in a collagen-coated culture dish followed by culturing in a low-calcium serum-free medium such as K-GM (Clonetics) or Keratinocyte-SFM (Gibco BRL) and replacing the medium every 2 weeks. After confirming that cells have proliferated, the cells adhered to the culture vessel are released and recovered by centrifugation followed by sub-culturing in serum-free medium.

Human dermal papilla cells are also obtained in the same manner as outer root sheath cells from human scalp obtained as by-products of plastic surgery procedures and surgery procedures under a stereo microscope. Next, the hair papilla are cultured in an ordinary animal cell culture medium such as Dulbecco's Modified Eagle Medium containing fetal calf serum and the medium is replaced every 2 days. After confirming that cells have proliferated, cells adhered to the culture vessel are released and recovered by centrifugation followed by sub-culturing in serum-free medium.

Immortalization of human outer root sheath cells or human dermal papilla cells obtained in this manner can be carried out by known methods. Preferably, the Large T antigen gene of SV40 virus deficient in a replication origin can be used as described in Japanese Unexamined Patent Publication No. 2000-89. This gene is normally used in a status being introduced in a plasmid or virus vector. This gene is widely used in the art as a typical gene for immortalizing animal cells and can be acquired easily. For example, a virus in which the EIA region in the adenovirus vector, ΔEI/X (Doren, et al., J. Virol., Vol. 50, 606-614 (1984)) is substituted with SV40 Large T antigen virus deficient in a replication starting point is described in Doren, et al., Mol. Cell. Biol., 1653-1656 (1984)). In addition, retrovirus vector pZITtsa (W. Filsell, et al., Journal of Cell Science, Vol. 107, 1761-1772 (1994)) can be used that is obtained by cleaving a 2491 by fragment containing a gene encoding temperature-sensitive polyomavirus Large T antigen (Plttsa) from pLTtsa (M. Rassoulzadegan, et al., Proc. Nat. Acad. Sci. USA, Vol. 80, 4354-4358 (1983) by use of BglI and HingII, and then inserting this fragment into a BamHI site of retrovirus vector pZIPNeoSV(X)l (C. L. Cepko, et al., Cell, Vol. 37, 1053-1062 (1984)). Moreover, pSV40ori-, obtained by cloning SV40 viral DNA deficient in a replication origin in pBR322, or pSHPV16s (Tissue Cult. Res. Commun., Vol. 11, 13-24 (1992)), obtained by cloning human papillomavirus type 16 DNA in pSV2neo vector, can also be used.

Prostate cancer cell line PC3 is a commercially available cell line that can be acquired from, for example, the American Type Culture Collection (ATCC) or DS Pharma Biomedical (formerly Dainippon Sumitomo Pharma).

Transformation of host cells can be carried out by a commonly known method such as the calcium chloride method, calcium phosphate coprecipitation, DEAE dextran method, lipofection, protoplast polyethylene fusion or electroporation, and a suitable method is selected according to the host cells to be used. In addition, a suitable commercially available kit can also be used to carry out transformation. Examples of such kits include Fugene® (Roche Applied Science), CombiMag (OZ Biosciences) and PolyMag (OZ Biosciences).

The resulting transformed host cells are cultured in a suitable culture medium, the cells are separated from the culture liquid by conventional means without limitation such as centrifugation or filtration, and cells are lysed as necessary, the protein component of the supernatant or filtrate is precipitated with a salt in the manner of ammonium sulfate, and the target protein can be recovered by carrying out various chromatographic techniques such as ion exchange chromatography or affinity chromatography.

The hair follicle formation induction activity of Wnt3a can be measured by using, for example, LEF-1 (lymphocyte enhancer factor 1), which is a factor for which gene expression is accelerated by the action of Wnt3a, as an indicator (Filali, M. et al., J. Biol. Chem., 277, 33398-33410, 2002). Wnt instructs cells so as not to decompose β-catenin ((β-CAT), and as a result, β-catenin binds with LEF-1 and similar proteins resulting in induction of hair follicle regeneration and hair growth. Confirmation of the expression of LEF-1 can be carried out by a commonly known method such as RT-PCR or Western blotting.

The following provides a more detailed explanation of the present invention through specific examples thereof. Furthermore, the present invention is not limited by these examples.

EXAMPLES

Construction of Wnt3a and Wnt7a Plasmids

The total length of human Wnt3a was amplified by PCR using cDNA synthesized from commercially available human placental total RNA (Clonetech) as a template and using a sense strand primer gatggccccactcggata (SEQ ID NO:2) and an antisense strand primer ggtgcctacttgcaggtgt (SEQ ID NO:3). Each amplified gene PCR product was purified with a commercially available kit (Promega), coupled to pTarget vector, and cloned using E. coli. After identifying the plasmids containing each gene based on an analysis of restrictase cleavage patterns, the nucleotide sequence of each inserted gene was determined using a DNA sequencer. The nucleotide sequence of the gene encoding Wnt3a is shown in FIG. 1.

Transfection into Cells

Each of the cells shown in the following Table 1 were seeded into a 6-well plate at 1 to $3 \times 10^5$ cells followed by culturing until the cells reached sub-confluency under conditions of 37° C. and 5% $CO_2$. Next, the constructed pTarget vector of Wnt3a or a control was transfected into the cultured cells using commercially available gene transfection reagents (Fugene® (Roche Applied Science), CombiMag (OZ Biosciences) and PolyMag (OZ Biosciences)). Which of the gene transfection reagents were used for which cells are as shown in Table 1. The transfection reagents were used in accordance with the protocol provided with each reagent. In addition, gene transfer efficiency was calculated by introducing a plasmid in which Azami Green gene (Medical & Biological Laboratories) was coupled to pTarget, followed by counting the number of cells positive for Azami Green fluorescence using a flow cytometer (Beckman Coulter). The medium, gene transfection reagent and results for transfer efficiency used for each cell are shown in Table 1.

TABLE 1

| Cell Name | Species | Origin | Gene Transfer Efficiency | Gene Transfection Reagent |
|---|---|---|---|---|
| IORS | Human | Immortalized outer root sheath cells | 25 | Fugene |
| hKC | Human | Epidermal keratinocytes | 8 | CombiMag |
| CEF | Chicken | Fetal fibroblasts | 10 | PolyMag |

TABLE 1-continued

| Cell Name | Species | Origin | Gene Transfer Efficiency | Gene Transfection Reagent |
|---|---|---|---|---|
| IDP | Human | Immortalized dermal papilla cells | 18 | PolyMag |
| HacaT | Human | Immortalized keratinocytes | 7 | PolyMag |
| Pam212 | Mouse | Squamous epithelial cells | 32 | PolyMag |
| PC3 | Human | Prostate cancer cells | 46 | Fugene |
| LNcap | Human | Prostate cancer cells | 10 | PolyMag |
| hFB | Human | Fibroblasts | 17 | Fugene |
| MCF7 | Human | Breast cancer cells | 0.8 | Fugene |
| Hela | Human | Cervical cancer cells | 0.3 | Fugene |
| mDC | Mouse | Dermal cells | 0.4 | Fugene |

As a result, Wnt3a gene was found to be introduced at comparatively high efficiency in IORS, IDP and PC3 cells.

Confirmation of Hyperexpression of mRNA by Wnt3a as Determined by RT-PCR

The constructed pTarget vector of Wnt3a or the control was introduced into IORS cells, and total RNA was extracted 2 days later using Isogen (Nippon Gene) to synthesize cDNA. Using the resulting cDNA of IORS cells as a template, a PCR reaction was carried out on human Wnt3a using a sense primer caggaactacgtggagatca (SEQ ID NO:4) and an antisense primer ccatcccaccaaactcgatg (SEQ ID NO:5), and hyperexpression was observed when expression of Wnt3a by the introduced plasmid was investigated (data not shown).

Confirmation of Expression of Recombinant Wnt3a Protein by Western Blotting

Cells transfected with each of the genes shown in Table 1 were lysed and subjected to heat treatment in SDS-polyacrylamide electrophoresis (SDS-PAGE) sample buffer 2 days after gene transfection followed by application to SDS-PAGE. At that time, samples were prepared so that the number of cells measured prior to protein extraction was equal between cells transfected with Wnt plasmid and the control vector. Next, protein was transferred from the gel following SDS-PAGE to a membrane using a semi-dry method. After treating the membrane with a commercially available blocking solution, the membrane was allowed to react with Wnt3a antibody (Abcam) diluted by 500-fold as the primary antibody. After washing with PBS-T, the membrane was allowed to further react with HRP-labeled anti-rabbit IgG (GE Healthcare Life Sciences) diluted by 2000-fold as the secondary antibody. Moreover, after washing with PBS-T, detection was carried out using ECL Advance (GE Healthcare Life Sciences). Commercially available mouse Wnt3a protein (R&D System) was used as a positive control. The results are shown in FIG. 2. High expression of Wnt3a was observed in IORS and IDP cells, and expression was also observed in PC3 cells.

Confirmation of Functional Expression of Introduced Wnt3a by Accelerated Expression of Lef-1

Whether or not Wnt3a hyperexpressed by introduction of a constructed plasmid functions physiologically was investigated by using Lef-1, which is a factor in which gene expression is accelerated by the action of Wnt (Filali, M. et al., J. Biol. Chem., 277, 33398-33410, 2002), as an indicator. The pTarget vector of Wnt3a plasmid or the control was introduced into IORS cells and total RNA was extracted 2 days later using Isogen (Nippon Gene) to synthesize cDNA. Using the resulting cDNA of the IORS cells as a template, a PCR reaction was carried out on human Lef-1 using a sense primer cttccttggtgaacgagtctg (SEQ ID NO:6) and an antisense primer gtgttctctggccttgtcgt (SEQ ID NO:7).

The results are shown in FIG. 3. In the case of having introduced Wnt3a plasmid, acceleration expression of Lef-1 gene was observed as compared with the control, and the introduced Wnt3a was determined to function physiologically.

The invention claimed is:

1. A PC3 cell transformed with an expression vector containing human Wnt3a gene.

2. The cell according to claim 1, wherein the expression vector is a mammalian expression T-vector.

* * * * *